United States Patent [19]

Weissman et al.

[11] Patent Number: 4,674,545
[45] Date of Patent: Jun. 23, 1987

[54] METHOD AND APPARATUS OF FORMING A FLEXIBLE DENTAL RETAINING SPLINT

[75] Inventors: Bernard Weissman, New York; Edmund Laviano, Bellport, both of N.Y.

[73] Assignee: IPCO Corporation, White Plains, N.Y.

[21] Appl. No.: 848,285

[22] Filed: Apr. 4, 1986

[51] Int. Cl.[4] ............................................. B21F 15/04
[52] U.S. Cl. .................................... 140/102; 140/71 R
[58] Field of Search ................ 140/3 A, 71 R, 71 C, 140/90, 93 R, 102, 113, 114, 115

[56] References Cited

U.S. PATENT DOCUMENTS

| 1,173,739 | 2/1916 | Rhenstrom | 140/71 R |
| 1,906,449 | 5/1933 | Dedrick et al. | 140/103 |
| 3,370,620 | 2/1968 | Stoeckel et al. | 140/113 |

Primary Examiner—Lowell A. Larson
Attorney, Agent, or Firm—Goodman & Teitelbaum

[57] ABSTRACT

An apparatus for forming a continuous length of flexible retaining splints including a plurality of body sections interconnected by eyelet sections. Each body section includes a number of core wires which are wire wrapped by a wrap wire. The eyelet sections include loops formed by at least one of the core wires. The apparatus includes a production zone into which the core wires are extended. Downstream of the production zone, at least one of the core wires is formed into a loop about a pin. The wrap wire is then wire wrapped about the extended core wires in the production zone. After completion of the wire wrapping, the loop is transferred from the downstream location to an upstream location where the loop is retained in place by another pin. This transfer also extends another portion of the core wires into the production zone to be wire wrapped. The process is repeated many times so that the continuous length of flexible retaining splints is formed.

20 Claims, 9 Drawing Figures

METHOD AND APPARATUS OF FORMING A FLEXIBLE DENTAL RETAINING SPLINT

BACKGROUND OF THE INVENTION

This invention relates to splint forming machines, and more particularly, to an apparatus which produces a flexible dental retaining splint of wire wound sections interconnected by eyelet sections.

A flexible dental retaining splint has been described in U.S. Pat. No. 4,332,563, assigned to the assignee of the present invention. The patented splint described is one which is disposable in a channel extending between adjacent teeth. The patented splint is formed of a wire core with a wire coil being wound about the core with the turns of the coil being in close juxtaposition to each other. Wire loops, or eyelets, are formed at both ends of the wound core. Typically, the patented splint is formed of several such sections of wire core, each of which is wire wrapped by a coil wire, and the eyelets serve as interconnections between the adjacent sections. Continuous strands of wire are utilized to form both the wire core sections, the wrapping wire, and the eyelets.

The patented splint can be bent along its longitudinal length into selected configurations, so as to fit into the channels formed in the teeth. The eyelets are transverse to the longitudinal sections and define apertures in the splint for receiving anchors that secure the splint in the channel.

The patented splint is provided as a continuous elongated unit having a plurality of individual sections. The elongated unit can be cut in order to fit the particular channel. The patented splint can then be bent so as to permit positioning of the splint for ideal pin placement into the dentin of the teeth. Once installed, suitable cement can be utilized to fill the channel, and then restorative material can be applied which can be contoured and polished to complete the restoration.

Although the wire splint described has been found to be exceedingly useful, formation of the splint requires a number of difficult procedures including bending of the wires wrapping the wires, and other similar operations, all of which must be accomplished using very thin wires. Typically, the wire is about 100 mm. stainless steel flexible wire strands. A complete splint may include a few sections of cores and eyelets and may extend up to approximately 4 inches. There is thus a need for a suitable method and apparatus for forming a flexible dental retaining splint of the aforementioned type described.

SUMMARY OF THE INVENTION

Accordingly, it is an object of the present invention to provide an apparatus for forming the aforementioned type of flexible dental retaining splint.

Another object of the present invention is to provide an apparatus which can form a plurality of interconnected flexible retaining splints, with each splint having a wire wrapped core section formed of wire strands, and having interconnecting eyelets formed of the same continuous wires which interconnect adjacent sections of the wire wrapped core.

A further object of the present invention is to provide an apparatus for forming a continuous length of a flexible retaining splint, which apparatus can be controlled by means of process controlled equipment.

Yet a further object of the present invention is to provide an apparatus for forming a continuous length of a flexible retaining splint having alternating wire wrapped core sections and looped sections, and wherein the wires forming the splint are retained in an untwisted condition throughout the length of the splint.

Still another object of the present invention is to provide an apparatus for forming a continuous length of a flexible retaining splint, wherein the splint is formed of continuous strands of wire suitably wound and bent to form a tight arrangement to permit bending of the splint.

Another object of the present invention is to provide a method for forming a continuous length of a flexible retaining splint of the type described in the aforementioned patent.

Briefly, in accordance with the present invention, an apparatus is provided for forming a continuous length of flexible retaining splint having a core section comprised of at least two core wires with a third wire being wrapped about the core wires, and having each core section interconnected to each other by eyelet sections formed by having the core wires coaxially looped while the wrap wire forms an arc section coaxial with the loops. The apparatus includes retractable retaining pins on which the eyelets are formed, and a rotatable member for wrapping the wrap wire about the core wires.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like references characters designate like parts.

DETAILED DESCRIPTION OF THE PREFERRED EMBODIMENT

Figure 1:
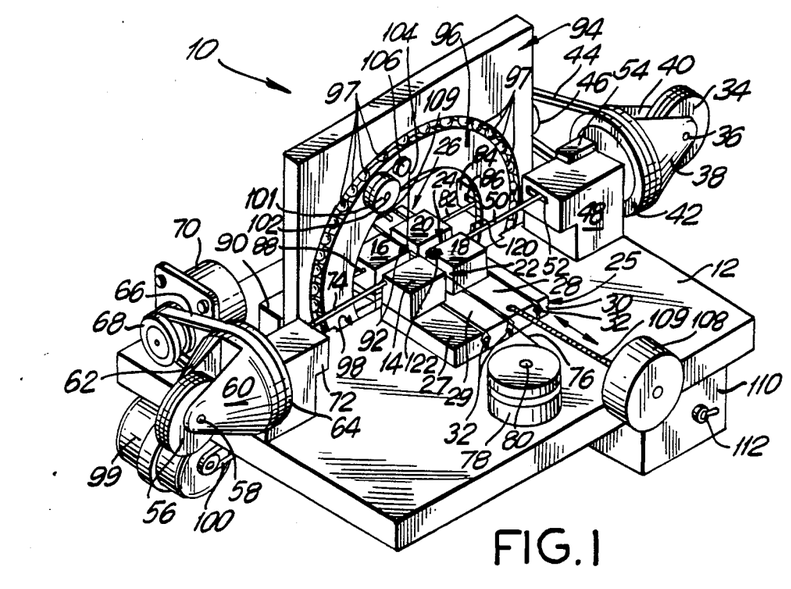
FIG. 1 is a perspective schematic view of the apparatus of the present invention for forming a flexible retaining splint.

Referring now to FIG. 1, the apparatus for forming the continuous length of flexible retaining splint is shown generally at 10, where it is understood that this is a schematic illustration with nonessential parts being omitted for a better showing thereof. The apparatus 10 includes a base plate 12 which supports the production mechanism. Four blocks 14, 16, 18, and 20 are orthogonally positioned to define orthogonal passageways therethrough. The first passageway 22 is referred to as the production passage, and the other passageway 24 is defined as the winding passage. Blocks 14 and 18 are mounted onto a support assembly 25 with a corresponding support assembly 26 being provided for the blocks 16 and 20. The support assemblies 25, 26 are spaced on opposite sides of the winding passageway 24, where the support assemblies 25, 26 are similar.

Each of the support assemblies 25, 26 includes a fixed support plate 27 which is secured to the base plate 12, the blocks 14 and 18 each being mounted on a separate support plate 27, and also includes a movable support plate 28 which can move transversely across the winding passageway 24, the blocks 16 and 20 each being mounted on a separate support plate 28 for movement therewith, as set forth below. Guild members 29, 30 are mounted on opposite sides of each support plate 28, with the guild member 29 being positioned adjacent to the fixed support plate 27. The guild members 29, 30 are secured to the base plate 12. Commercial ball bearing strip members 32 are disposed in V-shaped slots between the support plates 27, 28 and the guild members 29, 30 so that the support plate 28 can slide therebetween, as set forth below.

A first core wire is supplied by means of a wire supply spool 34 rotatably supported on a shaft 36 retained between an opposing pair of arms 38, 40 rearwardly extending from a wheel 42. A pulley belt 44 is connected to a pulley 46 operated by a motor (not shown) to rotate the wheel 42, which is similar to a motor arrangement on the opposite side of the base plate 12, as set forth below. Wire from the spool 34 extends through the center of the wheel 42 into the support block 48.

Extending from the opposite forward face of the support block 48 is a sleeve 50 which passes into the block 18 toward the production passage 22, as will hereinafter be explained. The first core wire from the spool 34 passes through the sleeve 50 for utilization in forming the splint, as will be explained below.

An elongated slot 52 is provided in the forward face of the support block 48 to permit transverse movement of the rod 50 when the block 18 and the support plate 28 thereof transversely move across the winding passageway 24. An electric solenoid 54 is provided on the support block 48 and operates to retract an inner pin supported within the rod 50, as will hereinafter be explained.

On the opposite end of the base plate 12, there is a second core wire supply spool 56, similarly rotatably supported by means of the shaft 58 and retained between the arms 60, 62 which extend rearwardly from a wheel 64. A pulley belt 66 is driven by means of the pulley 68 which is operated by means of a motor, shown generally at 70. It is noted, that the pulley 46 is similar to the pulley 68, where the pulley 46 is operated by a motor (not shown) similar to motor 70.

The wheel 64 is rotatably retained on a support block 72 having a rotatable rod or pin 74 extending from the opposite forward face thereof into the block 14, where the rod 74 is connected to the wheel 64 for rotation therewith. The wire from the second wire spool 56 passes coaxially through the center of the rod 74 for utilization in forming the splint, as will hereinafter be explained.

A third core wire 76 is provided from a third wire supply spool 78 which is mounted onto the base-plate 12 and rotatably retained by means of the center shaft 80 mounted onto the base plate 12.

A pin 82 extends into the block 20 from a support block 84. An elongated slot 86 is provided at the front face of the support block 84 to accommodate longitudinal movement of the block 20 and pin 82 with the support plate 28 along the base plate 12 by means of the ball bearing arrangement 32. A solenoid (not shown) contained within the support block 84 serves to retract and extend the pin 82, as will hereinafter be explained.

Another pin 88 is retained by support block 90 and passes through the block 16. A solenoid (not shown) in the support block 90 serves to retract and extend the pin 88, as will hereinafter be explained. An upwardly extending cam 92 is positioned at the front corner of the block 16 at the intersection of the orthogonal passageways 22, 24.

A support frame 94 upwardly extends from the base plate 12 and supports a disk shaped, press fit wheel 96 which is supported by ball bearings 97. The wheel 96 passes through an opening 98 formed in the base plate 12 the opening 98 is an extension of the passage 24. The wheel 96 is operated by means of an appropriate motor 99 and pulley belt 100. A wire supply spool 101 is mounted onto the wheel 96 by means of a shaft 102 and supplies a wrap wire 104. The wrap wire 104 is fed around a guide 106 to direct the wrap wire 104 downwardly towards the winding passage 24. As the wheel 96 rotates, the wrap wire 104 also rotates within the passage 24 to thereby wire wrap the core wires contained in the production passage 22, as will hereinafter be explained.

A motor 108 and a second similar motor (not shown) on the opposing side of the base plate 12 are the blocks 18, 20 thereon simultaneously between their respective fixed guild members 29, 30.

A rod 109 is connected between the motors 108 and the support plates 28 to provide the back and forth movement during operation of the motors 108. A main control box 110 is provided beneath the base plate 12, including an on/off switch 112 for turning on the apparatus 10. Contained within the control box 110 are suitable electronics, gearing, and other equipment, all conventionally known in the art, for causing the various motors and solenoids to operate. It should be appreciated, that an appropriate process control equipment could be included or connected to the apparatus 10 for controlling the various steps needed in the formation of the flexible retaining splint, these various steps will now be set forth below in detail.

Referring now to FIGS. 2-9, there is shown exploded perspective views of the four blocks 14, 16, 18 and 20 defining the orthogonal passageways 22 and 24 respectively serving as the production passage 22 and the winding passage 24. The view of the blocks in FIGS. 2-9 is a 90 degree clockwise rotation from that shown in FIG. 1.

Figure 2:
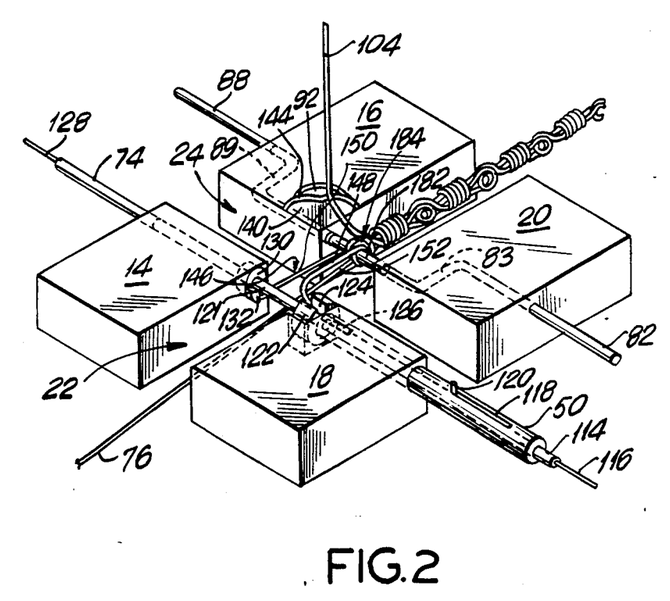
FIGS. 2-9 each show an enlarged perspective schematic view of the operating zone for forming the flexible retaining splint, and demonstrate the sequence of steps carried out by the apparatus in the formation of the flexible retaining splint, where nonessential parts have been omitted for a better showing thereof.
Figure 9:
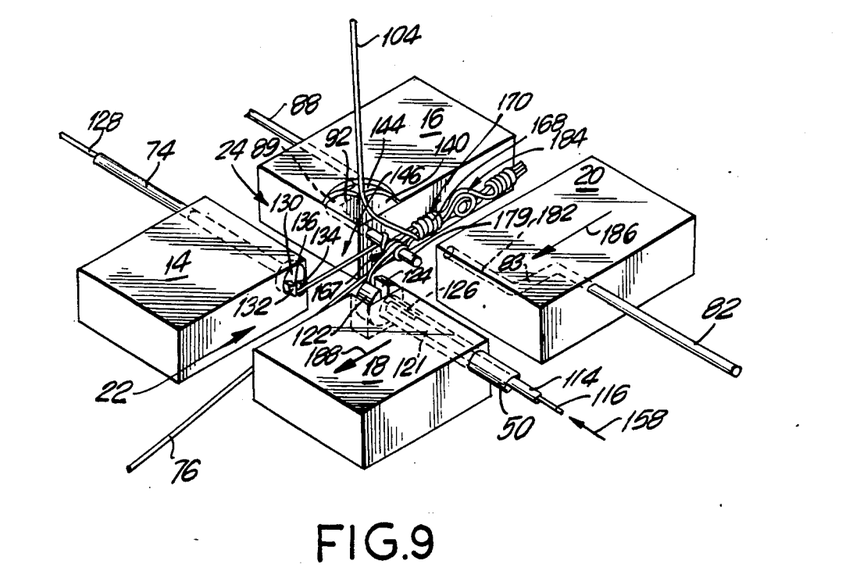

As shown in FIG. 2, the sleeve 50 supports therein a pin 114 which has a longitudinal center aperture for receiving therethrough the first core wire 116 fed from the spool 34. An elongated longitudinal slot 118 is formed along the sleeve 50 to receive the upwardly extending peg 120 projecting from the pin 114. Accordingly, the pin 114 can move axially within the sleeve to have its forward portion 121 extend transversely across the production passage 22. The pin 114 can be retracted by the length of the slot 118 so that the portion 121 is completely removed from the production passage 22, as shown in FIG. 9.

At the front distal end of the sleeve 50, there is provided an enlarged circular wheel 122 containing a notch 124 therein. An elongated slot 126 is formed in the pin 114 and an aperture (not shown) is provided in the pin 114 at the end of the longitudinal center aperture to permit the first core wire 116 to pass from the pin 114 through the slot 126 and extend across the notch 124.

The axial extension and retraction of the pin 114, as determined by the limits of the peg 120 within the slot 118 of the sleeve 50, is controlled by means of the solenoid 54, shown in FIG. 1. The rotation of the sleeve 50 and the wheel 122 thereon is controlled by means of the motor controlled wheel 42, shown in FIG. 1. The peg 120 is locked into the slot 118 to provide ganged rotation of both the pin 114 and the sleeve 50.

Rod or pin 74 extends through the block 114 and has a coaxial aperture therein to receive therethrough the second core wire 128 which is fed from the spool 56, shown in FIG. 1. At the distal end of the rod 74, there is provided a wheel 130 which can rotate within a correspondingly circular recess in the side of the block 14. On the face of the wheel 130, there is provided a pair of projecting portions 132, 134 defining a notch 136 therebetween, as best shown in FIGS. 6–9. An opening in the rod 74 permits the second core wire 128 to pass from the rod 74 and through the wheel 130 so as to extend through the notch 136. The rod 74 and the wheel 130 thereon are caused to rotate by means of the motor controlled wheel 64. It should be appreciated, that the pin 114 and the rod 74 are aligned with each other.

Figure 8:
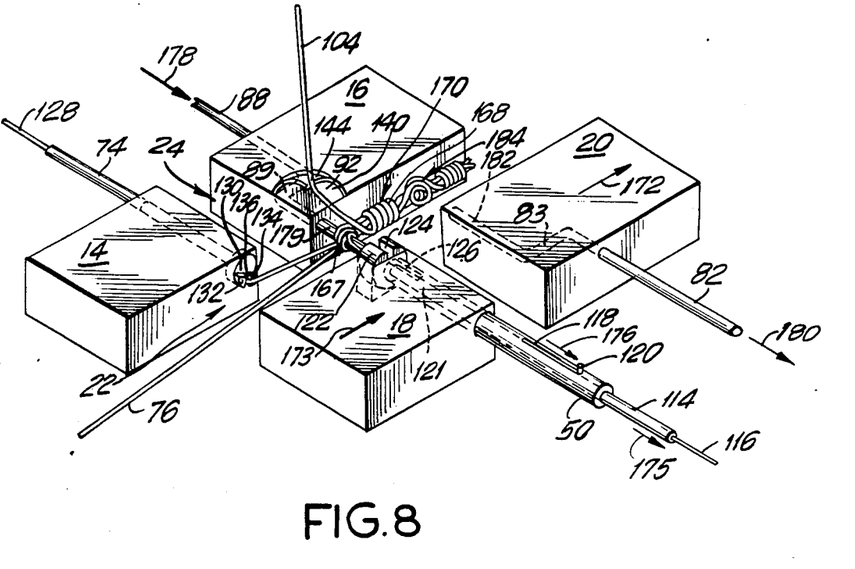

Pin 82 extends through the block 20 and has its axial movement controlled by means of a solenoid (not shown) contained in the support block 84. As a result, the pin 82 can extend across the production passage 22, as shown in FIG. 2, or be retracted within the block 20, as shown in FIGS. 8 and 9. The slot 86 in the block 84 permits the pin 82 to move back and forth with the block 20 along the base plate 12 when the support plate 28 is moved. It is noted, that for proper clearance and to provide the proper distance between the loops of the splint, the pin 82 is offset at 83 and the block 20 is provided with a recess (not shown) to permit the retraction of the pin 82.

Pin 88 extends through the block 16 and has its axial movement controlled by means of a solenoid (not shown) contained within the support block 90. The end of the pin 88 is aligned with the adjacent end of the pin 82, and can also move between an extended position where it traverses the production passage 22, as shown in FIGS. 8 and 9, or a retracted position within the block 16, as shown in FIG. 2. It is again noted, that for proper clearance and to provide the proper distance between the loops of the splint, the pin 88 is offset at 89 and the block 16 is provided with a recess (not shown) to permit the extension of the pin 88.

Guide 92 is shown having a front face 140 facing both the production passage 22 and the winding passage 24. The rear portion of guide 92 forms a sperical surface 144. The wrap wire 104 can pass along the front face 140 of the guide 92 as it moves between the passages 22, 24 where the guide 92 serves to hold the wire 104 taut as it guides the wire 104, as set forth below.

The intersection between the production passage 22 and the winding passage 24 forms a central production zone 146 in which the wire wrapping and core section of the splint are formed. The aligned pins 114 and 74 are positioned slightly downstream of the production zone 146, and the aligned pins 82 and 88 are positioned upstream of the production zone 146 and 20 are in alignment with each other to define a rectangular arrangement thereof, with the pins 82 and 114 extending across the production passage 22, and the pin 88 being in a retracted position.

In an arbitrary starting position, as shown in FIG. 2, the blocks 14, 16, 18 a section 148 of the first core wire 116, a section 150 of the second core wire 128, and a section 152 of the third core wire 76 are positioned in the production zone 146 with the ends of wire sections 148, 150 looped around the pin 82. Accordingly, the three wire sections 148, 150 and 152 serve as the three core wires to form a particular core section of the flexible splint. The wrap wire 104 is disposed upstream in the production passage 22.

The switch 112 is now turned on so that the various motors and solenoids of the apparatus 10 of FIG. 1 will operate to move the blocks, rods, wheels and pins in a proper sequence to form the splint, as set forth below.

Figure 3:
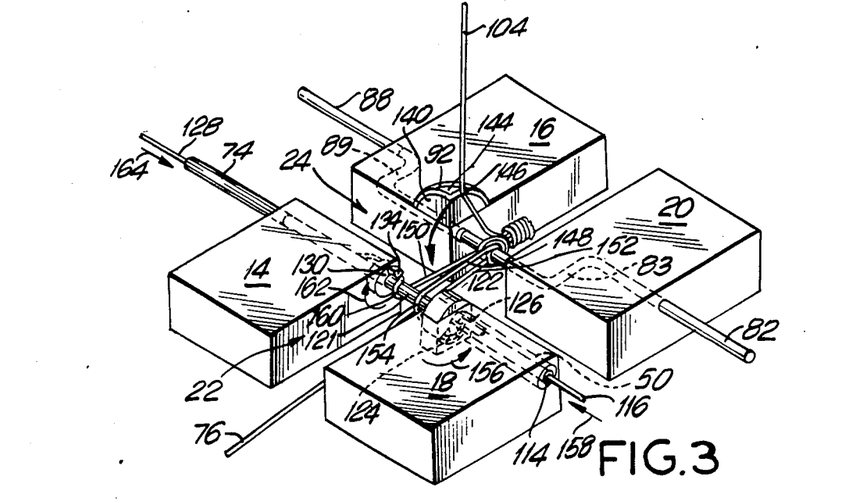

As shown in FIG. 3, the first step in the operation requires the rotation of the sleeve 50 together with its pin 114. This rotation, in the manner set forth above, causes the enlarged wheel 122 to rotate, whereby the first core wire 116 is grasped within the notch 124 so that the wire section 148 of the first core wire 116 forms a loop 154 about the extended portion 121 of the pin 114. The sleeve 50 and corresponding coaxial pin 114 are rotated in a counterclockwise direction, as shown by the arrow 156. As the core wire 116 is rotated, it causes the wire section 148 in the production zone 146 to become taut. Any extra core wire needed to form the loop 154 is pulled through the pin 114 along the direction shown by the arrow 158.

At the same time, the pin 74 and wheel 130 are also rotated, substantially simultaneous with the rotation of the pin 114 and sleeve 50. This rotation, in the manner set forth above, causes the wire section 150 of the second core wire 128 to be grasped within the notch 136 and to form another loop 160 about the extended portion 121 of the pin 114. The pin 74 and wheel 130 are rotated in a clockwise direction, as shown by the arrow 162. The formation of the loop 160 will cause the wire section 150 in the production zone 146 to become taut. Any additional core wire needed is pulled through the pin 74 along the direction shown by the arrow 164. The loop 154 of the first core wire 116 and the loop 160 of the second core wire 128 are coaxial since they are both looped about a common pin extension 121. The wire section 152 of the third core wire 76 is positioned in the production zone 146 as a pass wire without having any loop formed therein.

Figure 4:
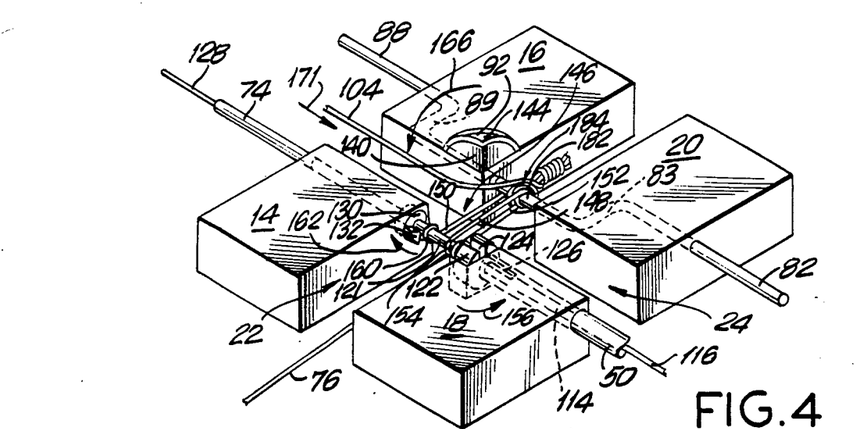

Referring now to FIG. 4, the next step involves the wire wrapping of the three core wire sections 148, 150 and 152 which now extend into the production zone 146. The wrap wire 104 is brought along the guide 92 to keep it taut, and then rotated through the winding passage 24 which is orthogonal to the production passage 22. The wrap wire 104 is wound in a counterclockwise direction, as shown by the arrow 166, by the rotation of the wheel 96 shown in FIG. 1. The wrap wire 104 is connected to a previously wound section, so that it is pulled over a portion of the loops of the previously formed section before it is rotatably wound, as will hereinafter be explained in more detail. As the winding proceeds, the wire section 152 of the core or pass wire 76 becomes pulled tightly closer to the other wire sections 148 and 150, so that it forms a semicircular arc about the pin extension 121, and with the loops 154, 160 forms an eyelet section 167 of the splint, as set forth below.

Figure 5:
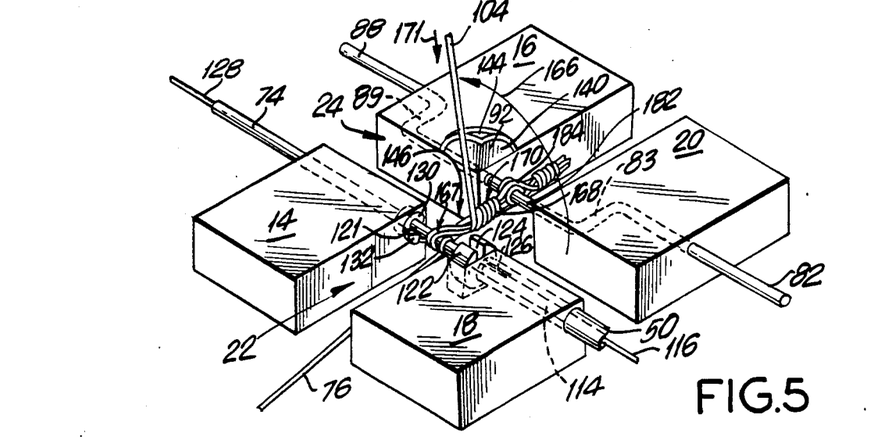

As shown in FIG. 5, the winding of the wrap wire 104 continues to form a tightly wound coil. Although the winding occurs along a single plane, a helical coil 168 of juxtaposed turns is wrapped around the three core wires to define a body section 170. A preselected number of turns is formed in order to provide a rigid structure for the body section 170. Any extra wrap wire needed to form the coil 168 is pulled from the supply spool 101, along the direction shown by the arrow 171, after passing over the guide 106 on the wheel 96 shown in FIG. 1.

Figure 6:
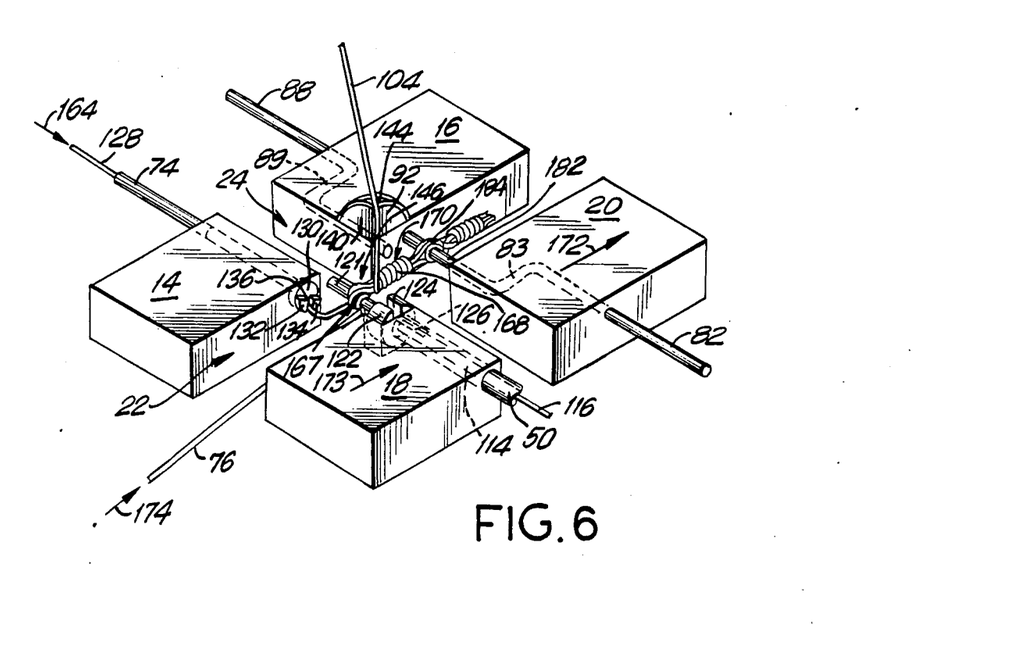

As shown in FIG. 6, after the wire wrapping has been completed, the wrap wire 104 is held in place and the two blocks 18, 20, on one side of the production passage 22, are moved longitudinally upstream, as shown by the arrows 172, 173. Such movement is facilitated by means of the ball bearing arrangements 32 which are disposed between the support plates 28, on which the block 18, 20 are mounted, and the guild members 29, 30 whereby the movement is controlled by the motors 108 and rods 109, as shown in FIG. 1.

As the blocks 18 and 20 move longitudinally simultaneously, the extended pin portion 121 moves out of alignment with the pin 74 and wheel 130, and proceeds to cross the the production zone 146 to move upstream. The wrap wire 104 begins to slide along the front face 140 of the guide 92 so as to maintain itself in a taut condition to prevent the wire coil 168 from becoming loose. As the block 18 moves, with the block 14 remaining stationary, some additional wire 128 of the second core wire is again pulled through the pin 74 in the direction of arrow 164 to begin providing a new section of the second core wire 128 which will be utilized to form the next body section. Similarly, the pass wire 76 is also pulled in the direction shown by the arrow 174 to begin the formation of a new section thereof to be also used in the formation of the next body section. As the block 20 is moved, the pin 82 moves out of alignment with the pin 88, and continues moving longitudinally along the production passage 22.

Figure 7:
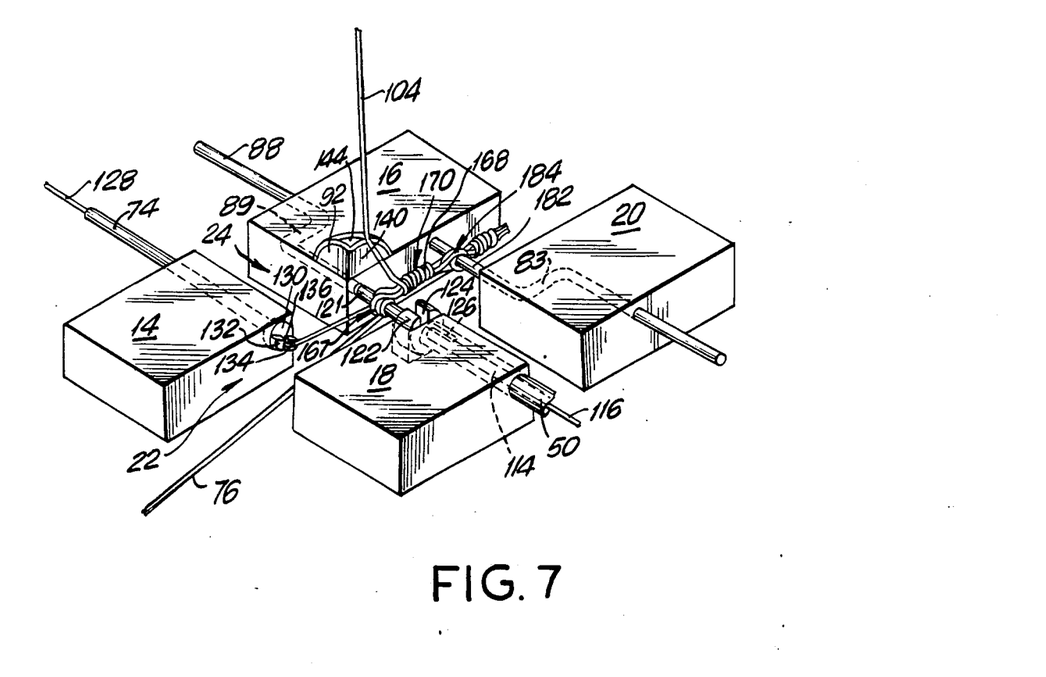

The longitudinal simultaneous movement of the blocks 18 and 20 continues until the pin section 121, extending from the block 18, has moved into the upstream position so that it is now in alignment with the upstream pin 88 which is retained in the block 16, as shown in FIG. 7. The wrap wire 104 is kept taut as it slides along the guide 92. The pin 82 has also now moved completely upstream along the production passage 22, and has maintained the same distance from the pin section 121 during this simultaneous movement.

As shown in FIG. 8, with the pin section 121 now in alignment with the pin 88, the pin 114 is now retracted from the sleeve 50 by the activation of the solenoid 54 of FIG. 1. This retraction distance is precisely determined by the pin peg 120 in the sleeve slot 118 so that the section 121 is completely retracted into the block 18. The pin 114 moves along the direction shown by the arrow 175, and the peg 120 moves along the same direction shown by the arrow 176. At the same time, the pin 88 is extending in the same direction shown by the arrow 178, being extended by the activation of the solenoid in the support block 90 of FIG. 1. Since the ends of these two pins are in alignment, the eyelet section 167 of the splint previously supported on the section 121 of pin 114 is now transferred onto the portion 179 of the pin 88 now extending into the production passage 22. As the pin 114 is being extracted, the peg 120 slides within the slot 118, with the sleeve 50 remaining stationary relative to the block 18.

Simultaneous with the extraction of the pin 114, the pin 82 is also extracted, as shown by the arrow 180, by the activation of the solenoid in the support block 84 of FIG. 1. Extraction of the pin 82, removes the pin portion 182 from the passage 22 and permits a previously formed eyelet section 184 of the splint to be further moved upstream along the production passage 22.

By means of the above transfer shown in FIGS. 6-8, completed body section 170 moved upstream from the production zone 146 so that new body sections can be wire wrapped in the above manner shown in FIGS. 4, 5. The previously formed eyelet section 167 of the splint is now retained in place on the pin portion 179 of the pin 88 at the upstream location.

As shown in FIG. 9, after the transfer of the eyelet section 167 has been completed, the blocks 18 and 20 are returned to their original positions by moving them back downstream, as shown by the arrows 186, 188. In moving downstream, the first core wire 116 is again pulled along the arrow 158 through the pin 114, thereby forming a new section of first core wire in the production passage 22.

When the blocks 18 and 20 have returned to their original positions, similar to that shown in FIG. 2, the pins 114 and 82 are now extended into the production passage 22. Simultaneously, the pin 88 is extracted from the production passage 22 back into the block 16 when the pin 82 is extended. In so doing, the eyelet section 167 of the splint just formed, now transfers from the portion 179 of pin 88 to the portion 182 of pin 82, where it will be held until the next movement time. At that time, the section 167 will again be moved upstream by the pin 82 and be completely disengaged free from the pin 82, in the manner set forth above. Pin 114 is now again extended to again provide the extended pin section 121 upon which new loops can be formed to define a new eyelet section, similar to that shown in FIG. 2. Accordingly, the production steps shown in FIGS. 3-9 will be repeated again and again to form additional body and eyelet sections of the splint.

Again referring to FIG. 1, it should now be appreciated that the solenoids serve to extend and retract the above mentioned associated pins 82, 88 and 114 into and out of the production passage 22. The motors, pulleys and belts serve to rotate the pins 74, 114 and sleeve 50, and the wheels 130, 122 connected thereto, respectively. By placing the spools 34 and 56 on the rotating wheels 42 and 64, the wires are permitted to rotate along with the pins 74, 114, thereby preventing the wires from twisting as the pins are rotated.

It should also be appreciated that since the block 18 moves horizontally to cross the winding passage 24, the frame 94 supporting the wheel 96 must be offset from the winding passage 24. Nevertheless, the wire 104 still extends from the supply spool 101 on the wheel 96 into the winding passage 24 by means of the guide 106 on the wheel 96 and the guide 92 provided on the block 16.

Accordingly, the particular sequence of above mentioned operating steps can be performed manually or can be electronically controlled by process control equipment, whereby the particular timing can be prearranged to move in the desired sequence heretofore described.

Although particular solenoids, motors and other conventional devices have been described, it should be apparent that alternate arrangements can be made to drive the various parts into the various sequential steps described above.

The particular flexible splint produced has continuous length body sections separated by eyelet sections, which can be cut into any desired lengths as required. Each of the body sections contains three core wires which are tightly wire wrapped by means of a wrap wire. Each of the eyelet sections contains two coaxial loops formed from two of the core wires. The loops are formed in opposite orientations, with one being clockwise and the other being counterclockwise. The loops are transverse to the longitudinal direction of the splint itself. The third core wire, serving as a pass wire, is not looped in the eyelet section, but only forms a coaxial arcuate section about the loops. Similarly, the wrap wire also forms an arcuate coaxial section about the loops on the opposite side from the pass wire.

The resulting splint is a substantially rigid, tightly formed construction. However, this construction permits flexibility in the bending and shaping of the splint to conform to a particular channel formed in the dentin. Additionally, by means of the eyelet sections, the splint can be retained in the channel with the eyelets receiving various anchor means, such as anchor pins, which can be screwed into the channel or the dentin itself.

Although three core wires were described, it should be understood that the number of core wires could be increased or decreased in number.

Numerous alterations of the structure herein disclosed will suggest themselves to those skilled in the art. However, it is to be understood that the present disclosure relates to a preferred embodiment of the invention, which is for purposes of illustration only, and it is not to be construed as a limitation of the present invention.

What is claimed is:

1. Apparatus for forming a length of a flexible retaining splint, comprising:
   (a) a base member having an elongated production passage through which moves a continuously produced retaining splint, a portion of said passage serving as a splint production zone;
   (b) first wire supply means for supplying at least one core wire into said zone;
   (c) second wire supply means for providing a wrap wire into said zone;
   (d) winding means for wire wrapping said wrap wire about a section of said one core wire within said zone;
   (e) production means downstream of said zone for forming at least one loop on said one core wire downstream of said zone;
   (f) retention means upstream of said zone for retaining said loop; and
   (g) transfer means for transferring said loop from said production means to said retention means, whereby each previously formed wire wrapped section and loop define a continuous length of retaining splints which is longitudinally moved upstream along said passage in a stepwise manner.

2. Apparatus as in claim 1, wherein third wire supply means supplies a second core wire into said zone to be wire wrapped, and wherein said production means forms at least one loop on said second core wire coaxially with said loop on said core wire.

3. Apparatus as in claim 3, wherein fourth wire supply means supplies a third core wire into said zone to be wire wrapped together with said one core wire and said second core wire.

4. Apparatus as in claim 1, wherein a winding passage is orthogonal to said production passage to intersect said production passage at said production zone, said winding means winding said wrap wire about said one core wire through said winding passage.

5. Apparatus as in claim 4, wherein four orthogonally located blocks define therebetween said production passage and said winding passage, said production zone being located at a center of said four blocks.

6. Apparatus as in claim 5, wherein said transfer means simultaneously moves two of said blocks disposed on one side of said production passage longitudinally with respect to the other two of said blocks disposed on the other side of said production passage.

7. Apparatus as in claim 5, wherein a raised cam surface is provided on a corner of one of said blocks located upstream of said production zone, said cam surface guiding said wrap wire from a completed wire wrapped section positioned upstream of said zone to said wire core section positioned in said zone for wire wrapping.

8. Apparatus as in claim 5, wherein said winding means includes a planar rotating disk extending around said four blocks, said second wire supply means being supported on said disk, and wherein a plane of said disk is upstream of said production zone to accommodate movement of one of said blocks across said winding passage.

9. Apparatus as in claim 1, wherein said production means includes a first retractable pin transversely extending across said production passage in a first position downstream from said production zone about which said one core wire is looped, said retention means including a second retractable pin for transversely extending across said production passage in a position upstream from said production zone, said transfer means longitudinally moving said first retractable pin from said downstream first position to an upstream second position into alignment with said second retractable pin when said second retractable pin is retracted and for subsequently returning said first retractable pin to said downstream first position, and sequentially retracting means for retracting said second retractable pin prior to movement of said first retractable pin to said upstream second position, and for simultaneously retracting said first retractable pin while simultaneously extending said second retractable pin once said transfer means have aligned said first and second pins, and for extending said first retractable pin after said transfer means have returned said first retractable pin to said downstream first position, so that a loop formed about said first retractable pin is transferred to said second retractable pin.

10. Apparatus as in claim 9, wherein said retention means includes a third retractable pin transversely extending across said production passage in a first position upstream of said production zone in alignment with said second retractable pin when said second retractable pin is in a retracted position, said transfer and retracting means moving said third retractable pin both longitudinally and transversely in concert with said first retractable pin, wherein said retracting means retracts said second retractable pin when said first and third retractable pins are being extended after return of said first retractable pin to said downstream first position, whereby said loop is transferred from said second retractable pin to said third retractable pin, and said third retractable pin stepwise moves said splint further upstream along said production passage.

11. Apparatus as in claim 9, wherein said production means includes a rotatable sleeve having an enlarged head portion at a distal end of said sleeve, said head portion being positioned adjacent said production passage, a notch is provided in said head portion, said first retractable pin being slidably received within said sleeve and extending out from said head portion in its extended position, said first retractable pin having an axial passageway therethrough for receiving said one core wire therein, an aperture provided in said first retractable pin so that said one core wire can extend out from said passageway of said first retractable pin to pass through said head portion notch, whereby rotation of said sleeve causes said head portion notch to loop said one core wire about an extended part of said first retractable pin.

12. Apparatus as in claim 11, wherein an elongated slot is provided longitudinally along said sleeve and a transverse peg extends from said first retractable pin to be slidably received in said slot for maintaining ganged rotational movement of said first retractable pin and said sleeve while permitting relative longitudinal movement therebetween.

13. Apparatus as in claim 11, wherein said production means further includes a rotatable pin at a downstream position in alignment with said first retractable pin, said rotatable pin having an axial passageway therethrough for receiving a second core wire therein, grasping means being provided at a distal end of said rotatable pin and positioned adjacent said production passage, whereby rotation of said rotatable pin causes said grasping means to loop said second core wire about said extended part of said first retractable pin.

14. A method of forming a flexible dental retaining splint having wire wrapped sections of core wire, the sections being interconnected by wire loops, said method comprising:
longitudinally extending a section of at least one core wire into a production zone;
forming a loop on said core wire downstream of said production zone;
providing a wrap wire into the production zone;
wire wrapping the wrap wire about the section of core wire;
transferring the loop of said core wire from the downstream location to a location upstream of the production zone to thereby longitudinally move the produced retaining splint in a stepwise manner; and
repeating the steps for the next section of core wire.

15. A method as in claim 14, and further comprising the steps of:
extending a second core wire into the production zone substantially parallel to the one core wire;
forming a loop on said second core wire downstream of said production zone in a coaxial arrangement with the loop of said one core wire;
wire wrapping the wrap wire about both said core wires; and
transferring both said loops of the core wires from the downstream location to the located upstream of the production zone.

16. A method as in claim 15, and further comprising the steps of:
extending a third core wire into the production zone substantially parallel to said first two core wires; and
wire wrapping the wrap wire about all three core wires.

17. A method as in claim 14, and further comprising the steps of:
extending a first pin transversely across the downstream location;
grasping the core wire adjacent to the first pin; and
turning the grasped core wire about the first pin to form the loop of core wire.

18. A method as in claim 17, and further comprising the steps of:
longitudinally moving the first pin from the downstream location to the location upstream;
withdrawing the first pin at the location upstream while simultaneously extending a second pin at the location upstream aligned with the first pin to transfer the loop from the first pin to the second pin;
returning the withdrawn first pin to the downstream location; and
again extending the first pin at the downstream location to receive another loop.

19. A method as in claim 18, and further comprising the steps of:
extending a third pin at the location upstream aligned with the second pin;
operating the third pin in concert with the first pin; and
withdrawing the third pin as the second pin is extended, whereby the loop received by the second pin is transferred to the third pin when the first pin is returned to the downstream location, and the loop on the third pin is longitudinally stepped along further upstream when the first pin is moved into alignment with the second pin.

20. A method as in claim 19, and further comprising the step of supplying the one core wire axially through at least a portion of the first pin.

* * * * *